United States Patent [19]
Milan et al.

[11] 3,945,372
[45] Mar. 23, 1976

[54] MEDICAL TISSUE-OBTAINING SYSTEM

[76] Inventors: Albert R. Milan, 1335 Heather Hill Road, Baltimore, Md. 21239; Raymond L. Markley, 707 Thornwood Court, Baltimore, Md. 21204

[22] Filed: Sept. 13, 1974

[21] Appl. No.: 505,709

Related U.S. Application Data

[63] Continuation of Ser. No. 365,850, June 1, 1973, abandoned.

[52] U.S. Cl. .............................. 128/2 B; 128/304
[51] Int. Cl.² ........................................ A61B 10/00
[58] Field of Search ........... 128/2 B, 2 W, 2 R, 304, 128/92 EC; 30/316; 401/122

[56] References Cited
UNITED STATES PATENTS

| | | | |
|---|---|---|---|
| 2,028,483 | 1/1936 | Van Yahres | 30/316 X |
| 2,591,927 | 4/1952 | Gladstone | 128/2 B |
| 2,839,049 | 6/1958 | Maclean | 128/2 B |
| 2,847,000 | 8/1958 | Nieburgs | 128/2 B |
| 2,850,007 | 9/1958 | Lingley | 128/2 B |
| 2,955,591 | 10/1960 | Maclean | 128/2 B |
| 3,485,236 | 12/1969 | Frost | 128/2 B |
| 3,491,747 | 1/1970 | Robinson | 128/2 B |
| 3,554,185 | 1/1971 | Kohl | 128/2 B |
| 3,626,946 | 12/1971 | Messey | 128/304 |
| 3,732,858 | 5/1973 | Banko | 128/2 B |

FOREIGN PATENTS OR APPLICATIONS

| | | | |
|---|---|---|---|
| 1,436,613 | 3/1966 | France | 401/122 |
| 343,830 | 6/1904 | France | 401/122 |
| 975,037 | 10/1950 | France | 401/122 |

OTHER PUBLICATIONS

Journ. of Bone & Joint Surgery, July, 1954, Vol. 36–A, p. 27.

*Primary Examiner*—Kyle L. Howell
*Attorney, Agent, or Firm*—Walter G. Finch

[57] ABSTRACT

An endometrial tissue-obtaining instrument includes a spiral section formed at one end of a flat plastic member and a handle portion at the other end. The spiral section is insertable into the womb of a female patient and rotated by the handle portion to remove endometrial tissue from the wall of the womb. The spiral section is withdrawn with the specimen of tissue.

The trailing portion of the spiral section is inserted into a slot of a plastic paddle and pulled away from the paddle so that the spiral section moves through the slot and is rotated thereby. The thickness of the slot permits the wiping, or extruding, of the tissue from the spiral section onto the paddle whereafter the paddle is manipulated to deposit the tissue onto a slide or stored for future purposes.

5 Claims, 7 Drawing Figures

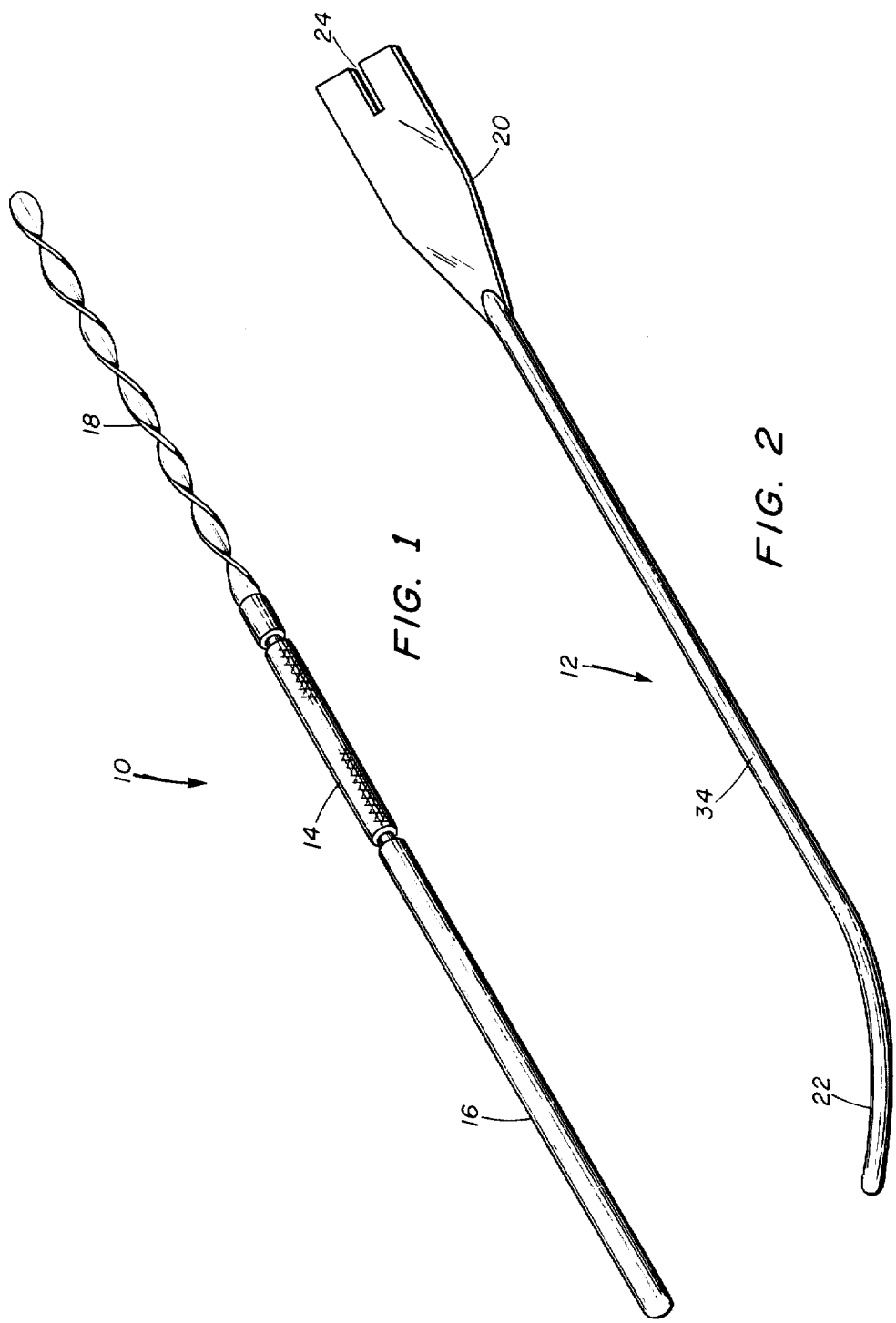

MEDICAL TISSUE-OBTAINING SYSTEM

This is a continuation of application Ser. No. 365,850, filed June 1, 1973, now abandoned.

This invention relates to a medical tissue-obtaining system and method of use thereof, and more particularly pertains to an instrument for obtaining and extracting tissue from the womb of a female patient and method of use of the instrument.

In the routine cytopathological evaluation of the cervicalvagina smear, the endocervical and endometrical components comprise a very small portion of the slide or may be completely absent. The postmenopausal mucous is usually very thick and tenacious, and essentially seals the endocervical canal thereby making it very difficult, and in many instances virtually impossible, for the effoliated endometrial cells to reach the vaginal pool. Consequently, these cells are rarely available in sufficient content when conducting a routine cervical-vaginal smear evaluation.

Thus, it becomes apparent that the use of the routine cervical-vaginal smear as a daily gynecological office procedure for determining pregnancy capabilities or for diagnosing endometrial neoplasia, or tumors, is inadequate.

There are several available techniques for the withdrawal of endometrial tissue for the purpose of determining pregnancy capabilities or for diagnosing endometrial neoplasia. However, these have proven to be complex, time consuming or have been of questionable diagnostic value. None of these have provided techniques which have met with minimum patient resistance and overall reliability coupled with economy of time and materials.

Some examples of these techniques are commonly referred to as brush techniques, aspiration techniques, and jet washing techniques. Most of these techniques depend upon suspension of the obtained specimen of endometrial mucous and cells being held in a solution to dissolve or separate unwanted substances and subsequent centrifugal separation. Paraffin embedding is also required and followed by the study of the resulting serial histological sections.

In the brush technique, a brush, having bristles extending radially from a central support, is inserted into the womb to engage the endometrial tissue. When the brush is withdrawn, tissue clings to the brush. Thereafter, the brush, with tissue clinging thereto, must be placed in a solution to dissolve the bristles thereby leaving the tissue in solution. A centrifugal, or filtering, process follows to separate the tissue from the solution. The tissue can then be analyzed.

The brush technique is time consuming and requires that each brush be dissolved which is costly. Also, the time delay between extraction of the tissue from the womb and ultimate analyzation thereof results in some loss in integrity of the tissue. This could provide less than desirable results in the ultimate tests.

In the jet washing technique, a saline solution is placed in a container, such as a syringe, which is inserted into the womb. A pressure reaction results as the container is removed and the endometrial tissue is drawn from the womb and brought out in the solution within the container.

Again the tissue must be separated from the solution. This is a time consuming process which adds to the cost of the test. Also the quality of the tissue specimen is lessened by the lapse in time before it is available for tests and, further, due to the necessity of subjecting the tissue to a filtration technique.

Another technique involves the use of a curette which is inserted into the womb to draw a sample of tissue from one area of the wall of the womb. This curette technique does not provide a single sampling of tissue from essentially all areas of the womb and is thereby limiting in its resultant effectiveness. Several samples must be taken from a single patient to obtain a reasonable cross section of the endometrial tissue which lines all areas of the wall of the womb. Even after all of this is done, there is no absolute assurance that sample tissue has been taken from all areas.

It becomes readily apparent, then, that the preparation, screening and final interpretation of these sections, obtained by presently available techniques, can be costly in terms of time and money. Further the material to be examined ultimately may be questionable and inadequate. If the material is not processed immediately, it becomes pale and washed out. Also, nuclear details are lost and osmotic artifacts may occur. This also means that a better-than-average skill is required to prepare readable slides and the cytologist must be deft at differentiating between artifact and real pathology.

Thus, there is a dire need for a technique which facilitates direct smearing of the endometrical mucous from the withdrawal instrument onto a slide with rapid fixation to prevent drying and osmotic artifacts. Such a technique would desirably provide a good cross section of the endometrial flora secured on a single slide. This technique would thereby provide a thorough sampling of endometrial tissue from essentially all areas of the wall of the womb and result in a complete examination thereof which is fast and economical.

It is an object of this invention, therefore, to provide a medical system, and a method of use thereof, for obtaining a tissue specimen from the womb which is representative of essentially an entire cross section of the womb.

Another object of this invention is to provide a medical instrument, and method of use thereof, which will permit the obtaining and withdrawal of endometrial tissue from the womb in a form which is uncontaminated by other substances.

Still another object of this invention is to provide a medical instrument and method and use thereof, which facilitates direct smearing of endometrial tissue as obtained from the instrument onto a slide with rapid fixation to prevent drying and osmotic artifacts.

A further object of this invention is to provide a medical instrument, and method of use thereof, for obtaining and analyzing endometrial tissue relatively quickly and less costly.

Still another object of this invention is to provide a medical instrument and accompanying implement, and method of use thereof, which permits the uncontaminated withdrawal of endometrial tissue from the womb by the instrument and transfer thereof to the implement for immediate transfer to an examination surface.

Yet another object is the provision of a medical instrument, and method of use thereof, for withdrawal of endometrial tissue from the womb of a patient in a relatively simple and efficient manner and in a nearly pain free, routine, gynecological-office procedure.

Other objects and attendant advantages of this invention will become more readily apparent and understood from the following detailed specification and accompanying drawings in which:

FIG. 1 is a pictorial view of a medical instrument having a spiral end section embodying certain principles of the invention;

FIG. 2 is a pictorial view of an implement used with the medical instrument of FIG. 1 in accordance with certain principles of the invention;

Figure 3:
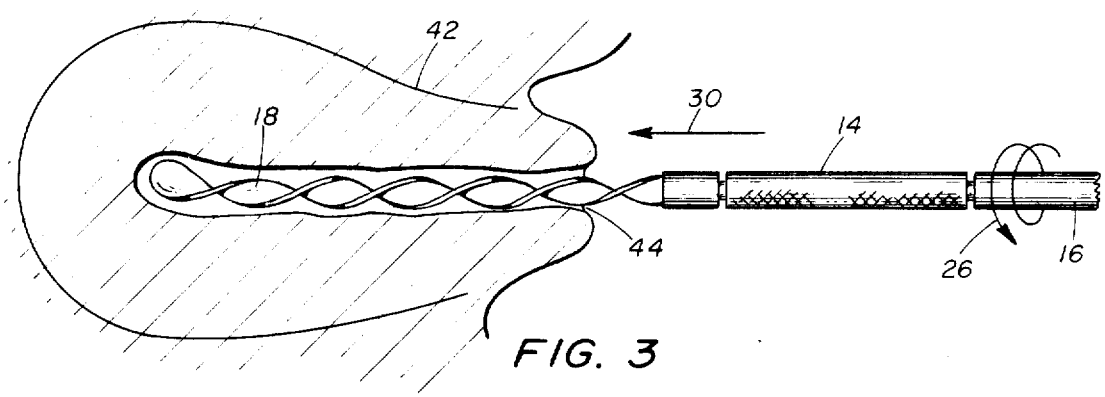
FIG. 3 is a partial section view showing the spiral end section of the instrument of FIG. 1 being inserted into the womb of a female patient.

A medical tissue-obtaining system is shown in the FIGS. Referring to FIG. 1, the system includes a medical instrument, such as a cytology curette instrument 10, which is formed with a spiral end section 18. The spiral end section 18 has the appearance of having been formed from a flat piece of material which has been twisted about its longitudinal axis. A rotatable sleeve 14 is used to connect a handle 16, in essentially axial alignment, with the spiral section 18. The sleeve 14 could be connected to the handle 16 and spiral section 18 by force fit or by threaded connection. This permits ready handling of the spiral section 18 without the necessity of direct contact after assembly with the sleeve 14 and handle 16.

The instrument 10 could be formed from a single piece of material with one end forming the spiral and the remaining or trailing portion forming the handle.

The spiral section 18 is composed of any suitable inert plastic material which is resilient, tough and pliable. The surface of the spiral section 18 is sand blasted to produce a matte surface. Additionally, the edges of the spiral section 18 are semi sharp and the longitudinal axis has a slight curvature. Subsequent to manufacture, the spiral section 18 is sterilized and packaged for shipment and handling, prior to use, without concern for contamination.

As shown is FIG. 2, the system further includes an extruder-dilator implement 12 which has a flat paddle 20 formed at one end and a curved portion 22 at the other end with an intermediate handle portion 34. The paddle 20 is formed with a slot 24. The width of the slot 24 is substantially equal to the thickness dimension of a flat portion of the spiral section 18 (FIG. 1). The opposing, longitudinal edges of the slot 24 are thinned so that the edges have a flexible wiper effect. The paddle 20 is also composed of an inert plastic material which is resilient, tough and pliable.

In use, the curved portion 22 of the implement 12 can be used to dilate the cervix, if needed, so that the instrument 10 can be moved in the direction of the arrow 30 where the spiral section 18 enters the womb 42 of a female patient through the entrance 44, and is thereby positioned within the endometrial cavity thereof. As noted, the long axis of the spiral sections 18 is designed with a slight curvature to facilitate passage of the section beyond the internal opening of the cervix. The leading end of the spiral section 18 is rounded to minimize any pain to the patient during insertion. Thereafter, the instrument 10 is rotated, as indicated by arrow 26, for example, for six to ten turns. The rotating spiral section 18 gathers in the tissue-containing mucous aggregate 28 (FIG. 4) from the walls of the womb 42.

Figure 4:
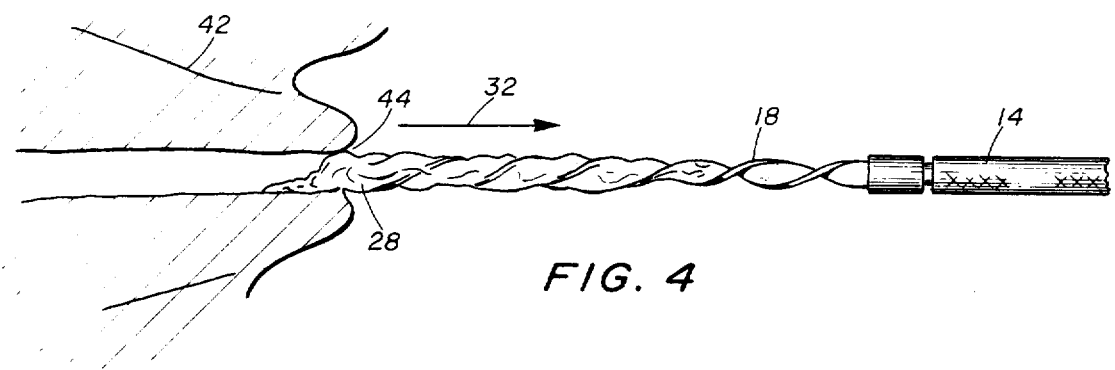
FIG. 4 is a partial section view, similar to FIG. 3, showing the withdrawal of the instrument from the womb with a tissue-containing, mucous aggregate.

The rotating spiral section 18 presents a multiple of scraping surfaces to the tissue within the endometrial cavity. This enhances the purpose of gathering a cross section of tissue from essentially all portions of the cavity in a single manipulation of the medical instrument 10. Upon withdrawal of the spiral section 18, continued rotation in combination with the semi-sharp edges of the spiral section 18 results in the endometrial cells on the surface of the walls of the womb 42 being curetted, or scraped, therefrom and into the mucous aggregate 28. Since the spiral section 18 is formed with a matte surface, the mucous aggregate 28 will adhere more readily and effectively thereto. Referring to FIG. 4, the instrument 10 is moved in the direction of the arrow 32 to withdraw the mucous-containing spiral section 18 from the womb 42.

The mucuous aggregate 28 is withdrawn with the spiral section 18 and provides in a simple, efficient and essentially painless manner, a cross section of endometrial tissue. Also some endocervical mucous is obtained upon withdrawal of the spiral section 18. This is accomplished by the unique design of the instrument 10 at the spiral section 18. The rotating of the instrument 10 permits essentially all areas of the wall of the womb 42 to be contacted with a complete cross section of endometrial tissue drawn onto the spiral section 18. As noted, the semi-sharp edges of the spiral section draw those cells closest to the surface of the wall of the womb 42. Thus, the instrument 10 not only provides a complete cross section of all areas of the womb 42 but also draws from the complete depth of the mucous aggregate 28 to obtain endometrial tissue which is immediately adjacent to the wall of the womb.

The techniques illustrated in FIGS. 3 and 4, and with the use of the instrument 10, is simple and nearly painless and can be conducted as a routine, daily gynecological office procedure. This, of course, reduces the comparative costs.

The endometrial tissue obtained by use of the instrument 10 is free of any contaminants and is only supported by the inert plastic spiral section 18. At this point, the tissue-containing mucous aggregate 28 is ready for transfer to an examining media so that the tissue may be studied for pregnancy related capabilities of the patient or for diagnosing endometrial neoplasia. While some of the mucous aggregate 28 could be wiped from the spiral section 18 onto an examining surface, such as a slide, it is desirable to remove substantially all of the mucous aggregate from the spiral section to provide sufficient tissue for the diagnostic specimen and also for histological studies.

Figure 5:
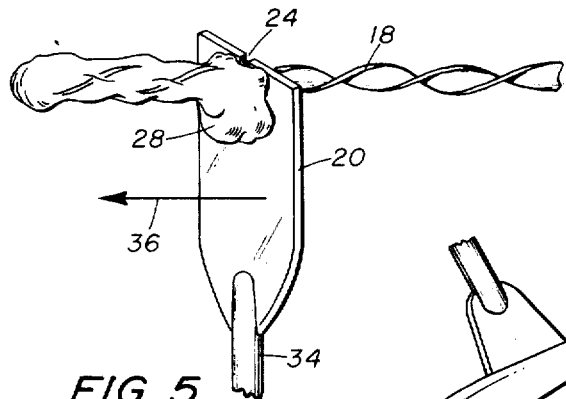
FIG. 5 is a pictorial view of a portion of the implement of FIG. 2 in temporary assembly with the tissue-containing spiral section of the instrument of FIG. 1 for the purpose of transferring the mucous aggregate from the instrument to the implement.

To effect the efficient and essentially complete removal of the mucous aggregate 28 from the spiral section 18, the rearwardmost portion of the spiral section is inserted into the slot 24 of the paddle 20 as shown in FIG. 5. The paddle 20 is moved slowly in the direction of the arrow 36, or the spiral section 18 is pulled slowly in the reverse direction, whereby the loosely held instrument 10 rotates. The rotation of the instrument 10 is caused by the spiral section 18 being forced through the slot 24

As the spiral section 18 moves through the slot 24, the mucous aggregate 28 is extruded, or wiped, from the spiral section and onto the paddle 20. The thin edges of the slot 24 provide a somewhat flexible wiper action which permits an essentially complete wiping of the mucous aggregate 28 from the spiral section 18. Subsequent to the removal of the mucous aggregate 28 from the spiral section 18, the relatively inexpensive section 18 is removed from the sleeve 14 and discarded.

Figure 6:
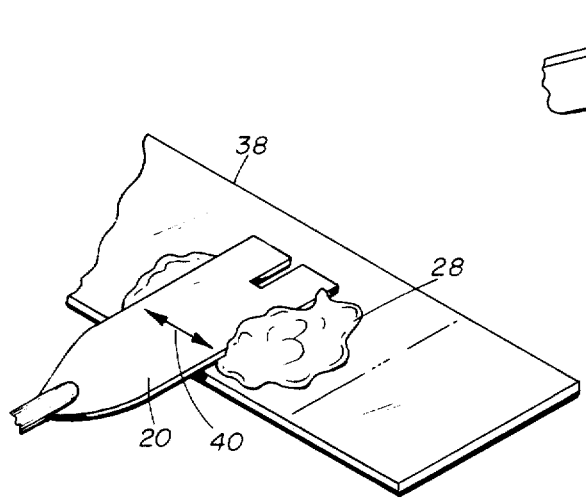
FIG. 6 is a pictorial view showing the transfer of the mucous aggregate from the implement of FIG. 2 to a slide.

Referring to FIG. 6, the paddle 20 is positioned to place the mucous aggregate 28 into engagement with a slide 38. Thereafter, the paddle 20 is moved back and forth as indicated by the arrows 40 to transfer an amount of the tissue-containing mucous aggregate 28 onto the slide 38 and spread the material evenly thereon.

The endometrial mucous is a thick, gliary, sticky substance and sometimes a swirling, or circular, motion of the paddle 20 is required to transfer the aggregate 28 evenly over the slide 38. The mucous aggregate 28 on the slide 38 should not be allowed to dry since drying results in a loss of significant histological and nuclear detail.

The slide 38 should be immediately placed in a jar containing Cornoy's solution so that any blood or debris which may be contained within the aggregate 28 is effectively cleared away. Thereafter, the slide 38 is removed from the Cornoy's solution and placed in a container of 95% alcohol which serves as a fixative. Other fixatives, such as aerosol spray fixatives, may be used if desired. However, due to the thickness of the endometrial mucous aggregate 28, the fixative of 95% alcohol appears to be the most effective.

Figure 7:
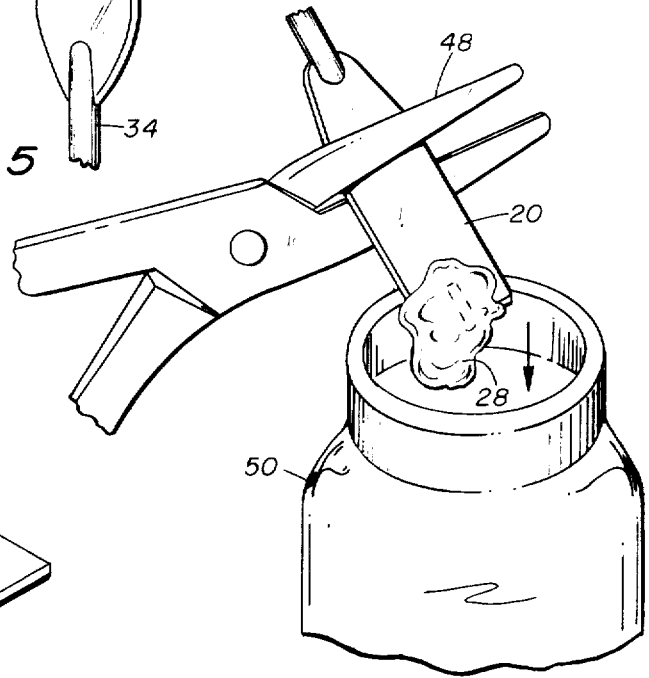
FIG. 7 is a pictorial view showing the depositing of the aggregate-supporting portion of the implement with the mucous aggregate into a container of 10% formalin.

As shown in FIG. 7, the remaining mucous aggregate 28 is gathered on the end of the paddle 20 which is the severed from the remaining portion thereof by the use of cutters 48. The severed, mucous-containing portion of the paddle 20 is dropped into a vial 50 containing 10% formalin. This remaining mucous aggregate 28 is usually sufficient for paraffin embedding and may be sufficiently large enough to provide enough tissue for a biopsy.

The spiral section 18 should be approximately 6 cm. in length while the most useful width is 3.5 mm. to 4.0 mm. The thickness of the spiral section 18 is about 0.75 mm. The diameter of the curved portion 22 and handle portion 34 of the implement 12 is about 3.5 mm. While these dimensions are representative of the disclosed embodiment, the invention may be practiced with many variations of dimensions to suit particular needs without departing from the spirit and scope of the invention.

Thus, the inventive medical instrument 10 and implement 12 facilitates an inventive and highly satisfactory method for obtaining direct smear tissues from endocervical and endometrial areas for the purpose of studying endometrial cytopathology. The use of this technique in comparison to other techniques, can be measured in the success of the adequacy of the endocervical and endometrial components, the quality of the slides and the clarity of cytoplasmic and nuclear detail. In addition, by using this technique, sufficient specimen is obtained to not only conduct the diagnostic tests but also for paraffin embedding and histological study. In some instances, enough additional specimen is obtained as biopsy material. All of these advantages are accomplished with a relatively simple, in-office, nearly painless procedure with the results being relatively quickly available and less costly.

Obviously many modifications and variations of the present invention are possible in light of the above teachings. It is, therefore, to be understood that within the scope of the appended claims the invention may be practiced otherwise than as specifically described.

What is claimed is:

1. A medical system for obtaining tissue samples, comprising: tissue gathering means including a helically-shaped end section, said end section being formed of a flat, elongated, and essentially rectangular member twisted about its longitudinal axis such that the edges thereof which extend in a direction parallel to the longitudinal axis of said member are disposed in a helically wound fashion about said longitudinal axis, the surface of the end section being of a matte finish to enhance adhesion of tissue thereon;

means for manipulating said gathering means and being joined to the inner end portion of said end section; and, a flat paddle-shaped member having a slot-like opening formed therein, at least a portion of the helically-shaped end section of the tissue gathering means being disposed within the slot-like opening and being movable relative thereto to transfer tissue adhering to the end section from said end section to a surface of the flat paddle-shaped member.

2. The medical system of claim 1 wherein the last-mentioned means is a rod-like handle member connected to and extending substantially axially of the end section of the gathering means.

3. The medical system of claim 1 wherein said opening is a slot having opposed side walls spaced apart a distance equal to at least the thickness of the edges of the end section.

4. The medical system of claim 3 wherein the slot is formed in one edge of the member, the helically shaped end section being disposed within the slot at the inner end of said section, the body portion of the end section being drawn toward the member to transfer tissue on said section onto that surface of the member opposite the direction of motion of the end section, the side walls of the slot acting to deposit the tissue on the member.

5. The medical system of claim 1 wherein the opening is defined by side walls of a reduced thickness relative to the remaining portions of the member, the side walls being flexible to provide a wiping action against surfaces of the end section moving relatively thereto to facilitate transfer of tissue on the end section from said end section to said member.

* * * * *